United States Patent [19]

Dutton

[11] Patent Number: 5,753,930
[45] Date of Patent: May 19, 1998

[54] DEVICE FOR TRANSLATING NEGATIVE FILM IMAGE TO A LINE SCAN

[75] Inventor: G. Wayne Dutton, Longmont, Colo.

[73] Assignee: The United States of America as represented by the United States Department of Energy, Washington, D.C.

[21] Appl. No.: 648,219

[22] Filed: May 17, 1996

[51] Int. Cl.$^6$ .................................................. G01N 21/22
[52] U.S. Cl. .............................. 250/559.02; 356/443
[58] Field of Search .................. 250/559.02; 356/443, 356/444

[56] References Cited

U.S. PATENT DOCUMENTS

| | | | |
|---|---|---|---|
| 1,850,909 | 3/1932 | Bahney. | |
| 3,127,508 | 3/1964 | Doty et al. | 235/181 |
| 3,503,689 | 3/1970 | Miller et al. | 356/203 |
| 3,556,664 | 1/1971 | Blaisdell et al. | 250/559.02 |
| 3,594,087 | 7/1971 | Miranda | 356/203 |
| 3,606,551 | 9/1971 | Becherer et al. | 356/203 |
| 3,663,110 | 5/1972 | Rising | 356/203 |
| 3,678,188 | 7/1972 | Okumura | 178/6.6 R |
| 3,705,755 | 12/1972 | Baer | 350/6 |
| 3,713,742 | 1/1973 | Goetz et al. | 356/206 |
| 3,883,251 | 5/1975 | Helava | 356/203 |
| 3,942,898 | 3/1976 | Anderson | 250/559.02 |
| 4,012,143 | 3/1977 | Buscher | 356/71 |

Primary Examiner—Stephone B. Allen
Attorney, Agent, or Firm—Earl H. Baugher, Jr.; James H. Chafin; William R. Moser

[57] ABSTRACT

A negative film reader records high-resolution optical density changes across negative film radiographic images to allow precise image dimensions to be determined. A laser light source capable of high-resolution focusing is passed through an intensity control filter, focused by a lens, and reflected off a mirror to focus in the plane of the negative film. The light transmitted through the film is collected by a second lens and directed to a photo diode detector which senses the transmitted intensity. The output of the photo diode signal amplifier is sent to the Y-axis input of an X-Y recorder. The film sample is transported in a plane perpendicular to the beam axis by means of a slide. The film position is monitored, with the signal amplified and recorded as the X-axis on the X-Y recorder. The linear dimensions and positions of image components can be determined by direct measurement of the amplified recording.

6 Claims, 1 Drawing Sheet

DEVICE FOR TRANSLATING NEGATIVE FILM IMAGE TO A LINE SCAN

The United States Government has rights in this invention pursuant to Contract No. DE-AC04-90DP62349 between the United States Department of Energy and EG&G Rocky Flats, Inc.

FIELD OF THE INVENTION

The present invention relates to high resolution negative film translators for precise recording of optical density changes across radiographic images. More particularly, the present invention is directed to devices that enable accurate measurement of the size or location of hidden holes, gaps or other features in components that have been radiographed.

BACKGROUND OF THE INVENTION

Testing for breakdown or deterioration of materials under exposure to a particular type of environment has greatly increased in recent years. Destructive testing means, such as tensile strength tests, are unacceptable for materials that are costly or difficult to fabricate, or that have been formed into finished or semi-finished products.

A number of different nondestructive tests have been used to detect cracks and flaws in the materials. External flaws can be located by ultrasonic inspection, magnetic testing, and covering the surface with a penetrating liquid detectable that is absorbed into the cracks and flaws rendering them readily visible when the surface is wiped. Internal as well as external flaws can be detected by x-ray or gamma radiation techniques in which the radiation passes through the material and impinges on a suitable photographic film. This process is commonly referred to as radiography. Under some circumstances, it is possible to focus the x-rays to a particular plane within the material, permitting a three dimensional description of the geometry as well as its location. Use of radiography in industrial applications permits nondestructive inspection of castings, welds and engineering structures.

Information regarding subsurface features received by these x-ray or gamma ray techniques can be recorded in the form of radiographs. The rays penetrate visually opaque materials to varying degrees to show up internal structures, thus allowing "pictures" to be produced on a sensitive surface, such as a negative film or a silver halide emulsion. This property makes radiographs useful in the nondestructive accurate measurement of the size or location of hidden holes, gaps or other features in components.

X-ray radiography involves the use of x-rays, which have wavelengths between one hundredth and one hundredth thousandth that of visible light. The x-rays are produced by high-voltage electron streams bombarding an electrode in a vacuum tube. The object to be recorded is placed between an x-ray tube and the film. The film registers the differential absorption of the x-rays by the objects internal structure as a projection shadow graph.

The technique of gamma ray radiography is similar to x-ray radiography but relies on rays emitted by radioactive substances. Gamma rays have wavelengths from one hundred to one thousand times shorter than x-rays, with a correspondingly greater penetration energy. Small gamma ray sources are placed in areas inaccessible to x-ray tubes, such as in pipelines. The exposed film is then developed to yield a negative film, also known as a radiograph.

The negative film records the image of the attenuation of an x-ray or gamma ray beam as it passes through an object. The x-ray or gamma ray transmission characteristic of the object under study, along a given ray direction, is presented as optical density at the corresponding point on the developed negative. This is analog information that can be interpreted by the radiographer in such terms as the quality and quantity of the materials of a weld, the presence of cracks and/or voids, or the quality of bonded materials. In many situations, a flaw in the x-rayed part becomes apparent in the film even to a casually trained observer. While in another film, there may be just a barest showing that is so marginal that even the expert radiographer is hard pressed to decide whether or not the part does in fact have an imperfection.

While the usual qualitative observation of radiographic film may quickly reveal most of the pertinent size related features of the radiographed object, it does not make full use of the transmission related information on the negative. The human brain, in spite of its remarkable function as a computer, does not permit the radiographer or other individual reading the film to recognize objects and discontinuities that have too low a contrast compared to their surrounding, nor does it register the film density quantitatively.

Some attempts have been made to determine the optical density of negative films and the like using various devices, including microdensitometers. U.S. Pat. No. 3,503,689 to Miller et al. is directed to a microdensitometer that displays photometric information in two-dimensions by creating two dimensional contour plots of equi-density lines. Two light beams are used, with one transmitted through the film and the other through a calibrated optical density transmission light wedge. A very similar device is shown in U.S. Pat. No. 3,606,551 to Becherer et al., in which isophotes, or lines of equal transparency, are created in two-dimensions. Another apparatus, described in U.S. Pat. No. 3,678,188 to Okumura, plots equi-density curves using a two-dimensional scanning device. However, none of these devices yield high-resolution dimensional measurements of imaged objects that can determine actual image dimensions for the X-Y recording of a line scan.

Another type of densitometer is shown in U.S. Pat. No. 3,594,087 to Miranda in which a broad beam scan is made of the media using a collimated non-laser extended source. To compensate for refraction problems caused by the film, a beam splitter is used so that two broad beams pass through the media. This does not enable precise image dimensions to be determined.

Other systems, such as that shown in U.S. Pat. No. 4,012,143 to Buscher, have digitized such data to accomplish image digital data compaction. This is to allow data to be stored in a compact form. For example, an E size engineering drawing can be reduced to the size of a 35 mm film aperture card.

It has now been discovered that a negative film reader in accordance with the present invention allows the precise, high resolution film optical density changes to be measured quantitatively, thus recording precise image dimensions.

SUMMARY OF THE INVENTION

The present invention is directed to a negative film reader for recording optical density changes across negative film images or radiographic images so that precise image dimensions can be recorded. This is useful in determining the size and location of flaws and cracks in a material.

The negative film reader operates by passing a coherent light beam, such as from a low-wattage laser, via various control and focusing means, through a negative film or radiographic image. The light transmitted through the film is collected and directed to a photo diode detector to sense the transmitted intensity. The output of the signal amplifier of the photo diode detector is sent to the Y-axis input of an X-Y recorder. The X-axis input to the X-Y recorder is the position of film as monitored by the linear slide holding the film.

From these inputs, and with proper calibration, the linear dimensions and positions of the image components can be determined by direct measurement of the amplified recording. Thus, the size or location of hidden holes, gaps or other features in components that have been radiographed can be accurately measured.

BRIEF DESCRIPTION OF THE DRAWING

The invention will be described with reference to the drawing, wherein.

DETAILED DESCRIPTION OF THE INVENTION

Figure 1:
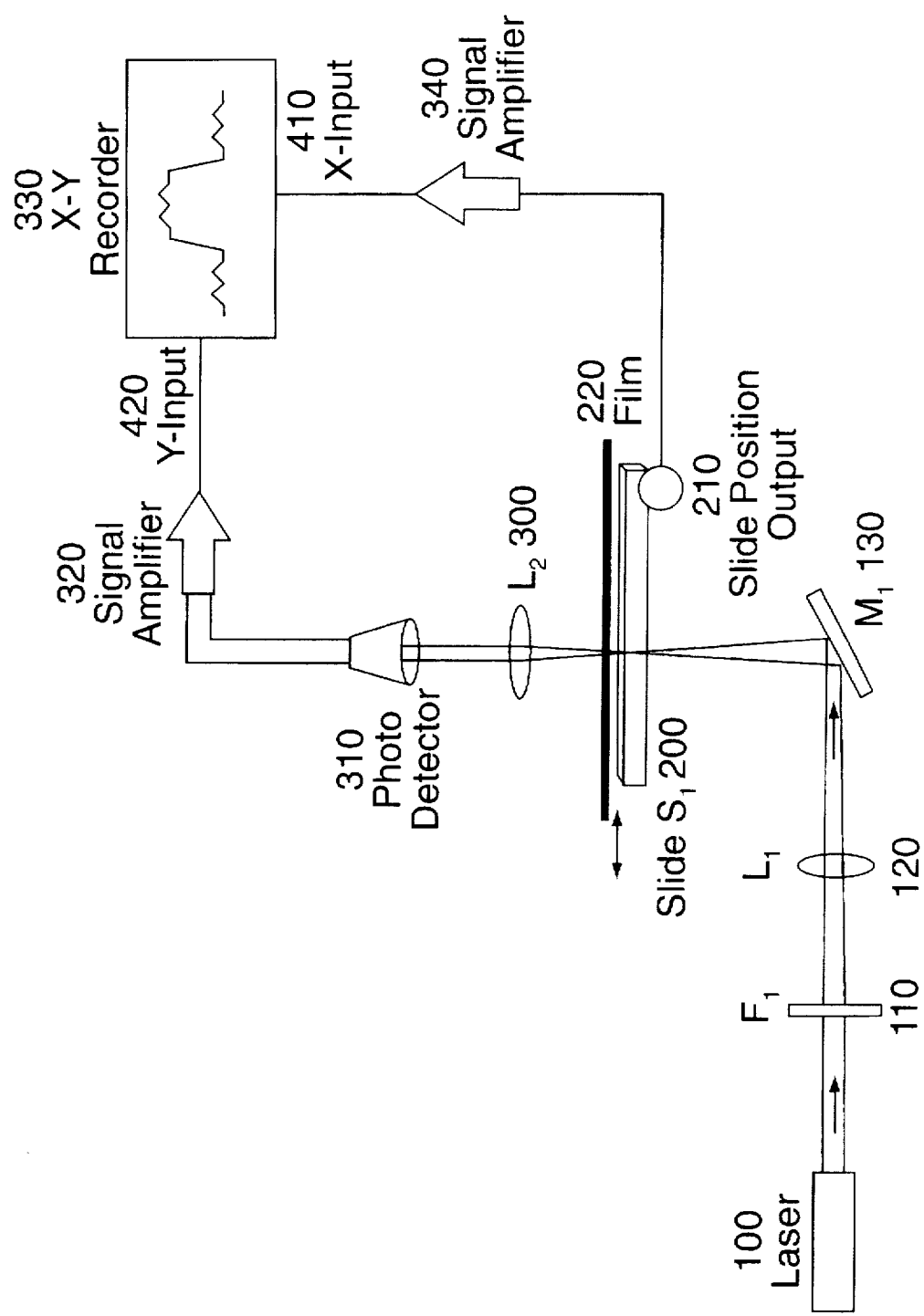
FIG. 1 is a schematic block diagram of the negative film translator of the present invention.

The present invention is directed to a negative film translator system which precisely measures the optical density of the film at each location on the film. From this information, the actual image dimensions can be determined.

The negative film reader system of the present invention is illustrated in FIG. 1, which is a schematic diagram of the preferred embodiment. The negative film translator 10 contains a moveable translation stage or slide 200 that the negative film 220 to be translator is placed on. Suitable securing means, not shown, are used to hold the negative film 220 in place during the reading operation. Drive motor means, not shown, are used for moving the stage so that another section of the negative film 220 can be translated. Slide position output means 210 sends the information regarding the amount of movement of the slide 200 and film 220 to the X-input 410 to X-Y recorder 330 to enable the image density readings to be correlated to the precise spot on the film 220 from which the reading was taken.

A low-wattage coherent and monochromatic laser light source 100 is used so that a high-resolution focusing of the light beam can be achieved. It is important that the light be coherent so that a high resolution image can be achieved. The use of a pulsed laser beam or an incandescent lamp will not allow for adequate focusing to render a precise translation of the optical density of the negative film. The light beam from laser 100 is directed from the laser along a light path to the film 220. The intensity of the light beam from laser 100 is controlled by means of filter 110. Lens 120 is used to collect the light beam from filter 110 and direct it to mirror 130, which focuses the light beam in the plane of the negative film 220. A second lens 300 collects the light transmitted through the negative film 220 and sends it to light receptive element 310. Light receptive element 310, which may be a photocell, photomultiplier or a photodiode, senses the intensity of the transmitted light beam and produces an electrical output, or signal, proportional to the intensity of that light. The signal from the light receptive element 310 is amplified by signal amplifier 320 and directed to the Y-input 420 of X-Y recorder 330. The X-Y recorder 330 records the direct image intensity for precise dimensional measurements on the object image.

In operation, the system is first calibrated to allow translations from different negative film images to be compared. Preferably, this is done so that the same optical density on negative film image will have the same magnitude on the Y scale of the X-Y recorder 330. The system may be calibrated by any suitable means. One means of calibration involves the use of a calibration negative film image with a known optical density. The calibration image may be uniform or may have a known gradient. The calibration negative film 220 is secured on the moveable translation stage or slide 200. The beam from the laser light source 100 is directed from the laser along a light path to the calibration film 220. The first lens 120 is adjusted so that the beam reflected from mirror 130 is focused in the plane of the calibration negative film 220. The second lens 300 is adjusted so that the light transmitted through the calibration negative film 220 is collected and sent to the light receptive element 310. Fine tuning of the optical density translations, as plotted on X-Y recorder 330, may be made by adjusting the filter 110 to regulate the intensity of the light beam from laser 100. Additional adjustments may be made by modifying the amplification of the signal in signal amplifier 320. Varying optical densities may be calibrated by using a gradient negative film image. Thus, with proper calibration, the direct image intensity can be plotted on the X-Y recorder so that precise dimensional measurements of the object image can be made.

In operation, the negative film 220 to be translated is placed on the moveable translation stage 200 and secured into place by any suitable securing means. The drive motor means, not shown, move the translation stage 200 to enable the entire negative film image 220 to be translated. The information regarding the specific section of the negative film 220 being translated is determined by slide position output means 210, which sends this information regarding the amount of movement of the slide 200 and film 220 to the X-input 410 to X-Y recorder 330. This enables the image density readings to be correlated to the precise spot on the film 220 from which the reading was taken.

During the translation operation, the light beam from laser 100 is directed from the laser along a light path to the film 220. The light beam from laser 100, the intensity of which was adjusted during the calibration process by means of filter 110, is collected by lens 120 and directed to mirror 130, to focus the light beam in the plane of the negative film 220. The second lens 300 then collects the light transmitted through the negative film 220 and conveys it to light receptive element 310. Light receptive element 310 senses the intensity of the transmitted light beam and produces an electrical output, or signal, proportional to the intensity of that light. The signal from the light receptive element 310 is amplified by signal amplifier 320 and directed to the Y-input 420 of X-Y recorder 330. At the same time, the drive motor moves the slide 200, the information regarding the slide position is transmitted to the X-input 410 of X-Y recorder 330 by slide position output means 210. Accordingly, the X-Y recorder 330 records the direct image intensity for precise dimensional measurements on the object image.

I claim:

1. A negative film translator device for determining the density of a negative film image, said device comprising:

a translation stage for holding film while said negative film image is being translated, said translation stage further comprising a means for advancing said film to expose a new portion of said negative film image;

means for determining the advancement of said film;

means for generating a signal proportional to the advancement of said film;

a monochromatic coherent light source for producing a laser beam;

means for directing and focusing said laser beam emanating from said light source onto said negative film image;

a light detection means for detecting the amount of light transmitted through said negative film image and for generating a signal proportional to the optical density of said negative film image; and an X-Y recorder, wherein the X-input is the signal proportional to the instantaneous optical density of said negative film image and the Y-input is the signal proportional to the advancement of said film so that a plot created by the X-Y recorder is of the optical density of said negative film image over said film.

2. The negative film translator device of claim 1 wherein said light detection means is a photodiode detector.

3. The negative film translator device of claim 1 wherein said means for directing and focusing said laser beam unto said negative film image is a filter and a lens.

4. A method of determining the optical density of a negative film image with respect to a location along an axis of a negative film image said method comprising the steps of:

securing said negative film image in a holding fixture so that a coherent light beam can be passed through said negative film image;

passing said coherent light beam through said negative film image;

moving said holding fixture along a first axis orthogonal to a second axis along which said coherent light beam is positioned, said first axis paralleling one edge of said negative film image;

receiving said coherent light beam and detecting the intensity of said coherent light beam transmitted through said negative film image;

generating a first signal proportional to the received intensity of said coherent light beam;

generating a second signal proportional to the instantaneous position of said negative film image along said first axis; and transmitting said first and second signals to a recording means and recording said first signal in relation to said second signal, wherein the intensity of said first signal is inversely proportional to the optical density of said negative film image and the instantaneous position of said first signal along said first axis is represented by said second signal.

5. A radiograghic negative film translator for high-resolution recording of optical density changes in two dimensions across radiographic negative film images and for determining precise image dimensions and the location of optical density changes within said image, said radiographic negative film translator comprising:

means for generating a monochromatic coherent light beam;

means for focusing and directing said coherent light beam in the plane of said radiographic negative film to be translated;

means for receiving and detecting said coherent light transmitted through said radiographic negative film image and generating a first signal proportional to the intensity of said coherent light;

means for holding said radiographic negative film image to be translated, wherein said film holding means allows the unimpeded transmission of coherent light through said radiographic negative film image;

means for moving said radiographic negative film image parallel to an edge of said negative film image along a first axis orthogonal to a second axis, said second axis being the axis along which said coherent light beam is transmitted through said radiographic negative film image;

means for establishing the instantaneous position of said radiographic film image along said first axis and for generating a second signal representing said instantaneous position; and means for recording said first and second signals as a graph of said coherent light beam's instantaneous intensity versus said radiographic negative film image's position along said second axis.

6. The device of claim 5 further comprising a signal amplification means for each of said first and second signals.

* * * * *